United States Patent [19]

Shimada et al.

[11] Patent Number: 5,449,800
[45] Date of Patent: Sep. 12, 1995

[54] SILICON-CONTAINING PENTACYCLIC COMPOUND, A SILICON-CONTAINING LADDER POLYMER, AND METHODS FOR PRODUCING THE SAME

[75] Inventors: Shigeru Shimada; Yuko Uchimaru; Masato Tanaka, all of Tsukuba, Japan

[73] Assignee: Director-General of Agency of Industrial Science and Technology, Tokyo, Japan

[21] Appl. No.: 363,814

[22] Filed: Dec. 27, 1994

[30] Foreign Application Priority Data

Dec. 27, 1993 [JP] Japan ................................. 5-353158

[51] Int. Cl.⁶ ............................. C07F 7/08; C07F 7/10
[52] U.S. Cl. ................................... 556/406; 556/11; 556/413; 556/423; 556/431; 549/214; 540/465; 540/476
[58] Field of Search ................ 556/431, 413, 423, 11, 556/406; 549/214; 540/465, 476

[56] References Cited

U.S. PATENT DOCUMENTS

| 4,826,984 | 5/1989 | Berlin et al. | 556/406 X |
| 5,143,993 | 9/1992 | Tour et al. | 556/406 X |
| 5,281,735 | 1/1994 | Rhein et al. | 556/406 |

OTHER PUBLICATIONS

M. Tanaka et al., Platinum-Complex-Catalyzed ..., Organometallics, vol. 10, No. 1, pp. 16–18, 1991.
M. Tanaka et al., Dehydrogenative double silylation ..., Bull. Soc. Chim. Fr., vol. 129, pp. 667–675, 1992.
Yuko Uchimaru et al., Platinum Complex-catalysed Polycondensation ..., J. Chem. Soc., Chem. Commun., pp. 744–745, 1993.
John F. Brown, Jr., Double Chain Polymers ..., Journal of Polymer Science, Part C, No. 1, pp. 83–97, 1963.

*Primary Examiner*—Paul F. Shaver
*Attorney, Agent, or Firm*—Birch, Stewart, Kolasch & Birch

[57] ABSTRACT

There is disclosed a method for effectively producing a silicon-containing pentacyclic compound, wherein the method comprises reacting (a) a 1,2-bis(hydrosilyl)benzene with (b) a cyclic diyne in the presence of (c) a platinum compound. There is also disclosed a method for effectively producing a silicon-containing ladder polymer having a complete ladder structure, wherein the method comprises reacting (a) a 1,2,4,5-tetrakis(hydrosilyl)benzene with (b) a cyclic diyne in the presence of (c) a platinum compound.

18 Claims, No Drawings

SILICON-CONTAINING PENTACYCLIC COMPOUND, A SILICON-CONTAINING LADDER POLYMER, AND METHODS FOR PRODUCING THE SAME

FIELD OF THE INVENTION

The present invention relates to a method for producing a silicon-containing pentacyclic compound useful as a raw material, for example, for a burning-resistant material, a thermal-resistant material, and an electrically conductive material. The present invention also relates to a novel silicon-containing pentacyclic compound obtained by the method. Further, the present invention relates to a method for producing silicon-containing ladder polymers having a complete ladder structure, which polymers are expected to be used as burning-resistant materials, thermal-resistant materials, electrically conductive materials, and nonlinear optical materials. The present invention also relates to novel silicon-containing ladder polymers obtained by the method.

BACKGROUND OF THE INVENTION

Hitherto, a silicon-containing pentacyclic compound represented by the formula:

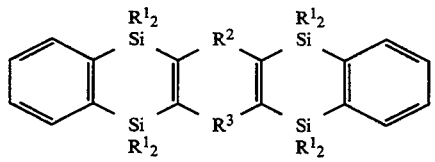

wherein $R^1$ represents a monovalent group, and $R^2$ and $R^3$ each represent a divalent group; and a method for producing it, have not been known.

While the main chain of conventional polymers consists of a single strand, the main chain of ladder polymers consists of a double strand. Therefore ladder polymers have long been expected to be excellent in thermal-resistance, mechanical strength, and chemical resistance. Further, in recent years, conjugation-type ladder polymers have been given attention as electronic material and nonlinear optical material. However, there is difficulty in using conventional techniques to produce polymers having a complete ladder structure. Recently, although several methods that use Diels-Alder reaction or the like have been reported (e.g., *Adv. Mater.*, 3, 282 (1991); and *Macromolecules*, 26, 5528 (1993)).

SUMMARY OF THE INVENTION

An object of the present invention is to provide a method of efficiently producing silicon-containing pentacyclic compounds by reacting, dehydrogenatively under mild conditions, 1,2-bis(hydrosilyl)benzenes and cyclic diynes, which are readily available raw materials.

Another object of the present invention is to provide novel silicon-containing pentacyclic compounds obtained by the above method.

Still another object of the present invention is to provide a method of efficiently producing silicon-containing ladder polymers having a complete ladder structure by reacting, dehydrogenatively under mild conditions, 1,2,4,5-tetrakis(hydrosilyl)benzenes and cyclic diynes, which are readily available raw materials.

Further, still another object of the present invention is to provide novel silicon-containing ladder polymers obtained by the above method.

Other and further objects, features, and advantages of the invention will appear more fully from the following description.

DETAILED DESCRIPTION OF THE INVENTION

The present inventors, having studied keenly to attain the above objects, have found that specific 1,2-bis(hydrosilyl)benzenes and specific cyclic diynes interact quickly under mild conditions in the presence of a platinum compound, to give silicon-containing pentacyclic compounds.

Further, the present inventors have found that specific 1,2,4,5-tetrakis(hydrosilyl)benzenes and specific cyclic diynes interact quickly under mild conditions in the presence of a platinum compound, to give silicon-containing ladder polymers having a complete ladder structure. The present invention has been completed based on these findings.

That is, the present invention relates to:

(1) A method for producing a silicon-containing pentacyclic compound represented by the following formula (III), which method comprises reacting (a) 1,2-bis(hydrosilyl)benzene, represented by the following formula (I), with (b) cyclic diyne, represented by the following formula (II), in the presence of (c) a platinum compound:

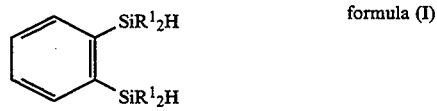
formula (I)

wherein $R^1$ represents a monovalent group;

formula (II)

wherein $R^2$ and $R^3$ each represent a divalent group;

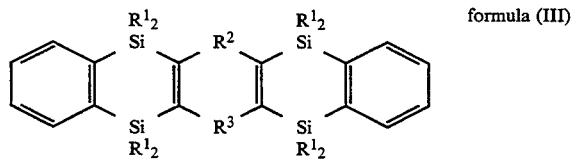
formula (III)

wherein $R^1$ $R^2$ and $R^3$ have the same meanings as defined above (hereinafter this method is referred to as the first invention); and (2) A method for producing silicon-containing ladder polymers represented by the following formula (V), which method comprises reacting (a) 1,2,4,5-tetrakis(hydrosilyl)benzene, represented by the following formula (IV), with (b) cyclic diyne, represented by the following formula (II), in the presence of (c) a platinum compound:

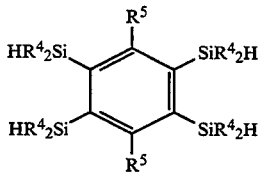

formula (IV)

wherein $R^4$ and $R^5$ each represent a monovalent group;

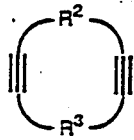

formula (II)

wherein $R^2$ and $R^3$ each represent a divalent group;

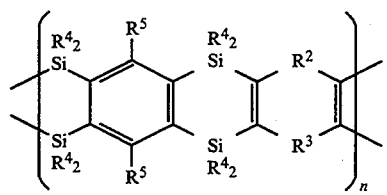

formula (V)

wherein $R^2$, $R^3$, $R^4$, and $R^5$ have the same meanings as defined above, and n is a positive integer (hereinafter this method is referred to as the second invention).

The present invention also relates to compounds represented by the above formulae (III) or (V).

In the methods of the present invention (the first and second inventions), it is considered that the reaction proceeds as follows:

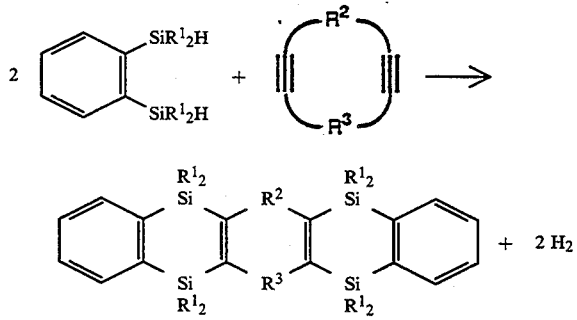

wherein $R^1$, $R^2$, and $R^3$ have the same meanings as defined above, or

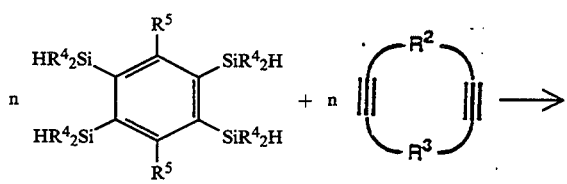

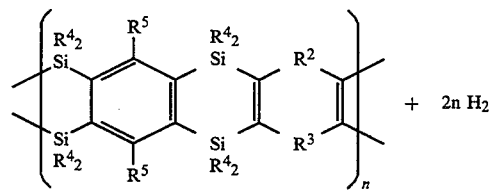

wherein $R^2$, $R^3$, $R^4$, $R^5$, and n have the same respective meanings as defined above.

In the above process scheme, n is a positive integer, preferably in the range of 1 to 20,000, more preferably 3 to 2,000.

The 1,2-bis(hydrosilyl)benzenes for use in the first invention are represented by the formula (I):

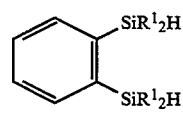

formula (I)

In the formula (I), $R^1$ represents a monovalent group, such as an alkyl group having 1 to 12 carbon atoms, an aryl group, an aralkyl group, and an alkoxy group. Examples of the 1,2-bis(hydrosilyl)benzenes represented by formula (I) having such a substituent that can be mentioned are 1,2-bis(dimethylsilyl)benzene, 1,2-bis(diethylsilyl)benzene, 1,2-bis(dihexylsilyl)benzene, 1,2-bis(diphenylsilyl)benzene, 1,2-bis(dibenzylsilyl)benzene, 1,2-bis(dimethoxysilyl)benzene, and 1,2-bis(diisopropoxylsilyl)benzene.

The cyclic diynes for use in the first and second inventions of the present invention are presented by the formula (II):

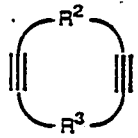

formula (II)

In the formula (II), $R^2$ and $R^3$ each independently represent a divalent group, such as an alkylene group, an arylene group, an aralkylene group, $-CH_2OCH_2-$, $-CH_2CH_2OCH_2CH_2-$, $-CH_2OCH_2CH_2OCH_2-$, $-CH_2OCH_2CH_2OCH_2CH_2OCH_2-$, $-CH_2NRCH_2-$, $-(CH_3)_2Si-O-Si(CH_3)_2-$, and a 1,1'-ferrocenylene group. Examples of the cyclic diynes represented by formula (II) and having these substituents that can be mentioned are 1,8-cyclotetradecadiyne, 1,8-cyclopentadecadiyne, 1,5-cycloundecadiyne, oxacyclotetradeca-4,11-diyne, 1,6-diisopropyl-1,6-diazacyclodeca-3,8-diyne, 5,6,11,12-tetradehydrodibenzo[a,e]-cyclooctene, 2,2,5,5,7,7,10,10-octamethyl-1,6-dioxa-2,5,7,10-tetrasilacyclodeca-3,8-diyne, [2,2]ferrocenophane-1,13-diyne, and 7,8,12,13-tetradehydro-9H,11H-naphtho[1,8-ef]oxecin.

The 1,2,4,5-tetrakis(hydrosilyl)benzenes for use in the second invention of the present invention are represented by the formula (IV):

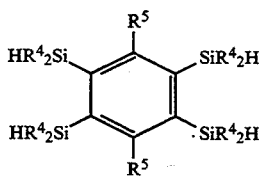

formula (IV)

In the formula (IV), $R^4$ and $R^5$ each independently represent a monovalent group. Examples of $R^4$ are an alkyl group having 1 to 12 carbon atoms, an aryl group, and an aralkyl group; and examples of $R^5$ are a hydrogen atom, an alkyl group having 1 to 20 carbon atoms, an aryl group, an aralkyl group, an alkoxy group, an alkoxymethyl group, and an alkenyl group. Examples of the 1,2,4,5-tetrakis(hydrosilyl)benzenes represented by formula (IV) having these substituents that can be mentioned are 1,2,4,5-tetrakis(dimethylsilyl)benzene, 1,2,4,5-tetrakis(diethylsilyl)benzene, 1,2,4,5-tetrakis(dihexylsilyl)benzene, 3,6-dimethyl-1,2,4,5-tetrakis(dimethylsilyl)benzene, 3,6-dioctyl-1,2,4,5-tetrakis(dimethylsilyl)benzene, 3,6-dioctyloxy-1,2,4,5-tetrakis(dimethylsilyl)benzene, and 3,6-bis[(octyloxy)methyl]1,2,4,5-tetrakis(dimethylsilyl)benzene.

In the production process of the first invention, the molar ratio of the 1,2-bis(hydrosilyl)benzenes to the cyclic diynes, which are respective raw materials for the reaction, is preferably in the range of 1:50 to 100:1, more preferably 2:5 to 5:1. In that of the second invention, the molar ratio of the 1,2,4,5-tetrakis(hydrosilyl)benzenes to the cyclic diynes, which are respective raw materials for the reaction, is preferably in the range of 1:100 to 200:1, more preferably 1:5 to 5:1.

As the platinum compound for use as a catalyst in the production processes of the first and second inventions, conventionally known various platinum catalysts can be used. In the present invention, compounds that are at least partly soluble in the reaction system are preferable, in view of the reaction rate. Out of those compounds, platinum complexes containing organic ligands are particularly preferably used. Examples of the ligands contained in the platinum complexes used in the present invention that can be mentioned are a phosphine, a phosphonite, a phosphinite, a phosphite, an olefin, acetylene, a β-diketonato ligand, a conjugated ketone, an amine, and carbon monoxide. Specific examples that can be mentioned are chain phosphines, such as trimethylphosphine, tributylphosphine, triethylphosphine, tricyclohexylphosphine, triphenylphosphine, tri(p-tolyl)phosphine, tri(p-anisyl)phosphine, diphenylmethylphosphine, and phenyldimethylphosphine, cyclic phosphines, such as P-methylphospholene, P-methylphosphole, and 9-methyl-9-phosphabicyclo[4,2,1]nonane, bisphosphines, such as 1,2-bis(dimethylphosphino)ethane, 1,3-bis(dimethylphosphino)propane, 1,4-bis(dimethylphosphino)butane, 1,2-bis(diphenylphosphino)ethane, 1,3-bis(diphenylphosphino)propane, 1,4-bis(diphenylphosphino)butane, 1,1'-bis(dimethylphosphino)ferrocene, 1,1'-bis(diphenylphosphino)ferrocene, α,α-bis(dimethylphosphino)-o-xylene, and 1,2-bis(dimethylphosphino)benzene, phosphonites, such as dimethyl methylphosphonite and dimethyl phenylphosphonite, phosphinites, such as methyl dimethylphosphinite and phenyl diphenylphosphinite, phosphites, such as triethyl phosphite, triphenyl phosphite, and 1-phospha-2,6,7-trioxa-4-ethylbicyclo[2,2,2]octane, olefins and dienes, such as, ethylene, propene, cyclooctene, maleic anhydride, 1,5-hexadiene, 1,5-cyclooctadiene, 1,3-cyclopentadiene, 2,5-norbornadiene, and 1,3,5,7-cyclooctatetraene, β-diketonato ligands, such as acetylacetonato, conjugated dienes, such as dibenzylideneacetone, amines, such as ethylenediamine and 2,2'-bipyridyl, and carbon monoxide. Specific examples of the platinum compound used in the present invention that can be mentioned are, therefore, (η-ethylene)bis(triphenylphoisphine)platinum, tetrakis(diphenylmethylphosphine)platinum, dichlorobis(phenyldimethylphosphine)platinum, chlorohydridebis(tributylphosphine)platinum, dichloro(tetramethylethylenediamine)platinum, dibromobis(triethylphosphite)platinum, bis(η-1,5-cyclooctadiene)platinum, dichloro(η-1,5-cyclooctadiene)platinum, dicarbonylbis(tributylphosphine)platinum, carbonatobis(tricyclohexylphosphine)platinum, bis(dibenzylideneacetone)bis(triphenylphosphine)platinum, and bis(dibenzylideneacetone)platinum, but the present invention is not limited to them.

These platinum compounds may be used not only singly but also in combination of two or more. A mode in which the platinum compound is used in combination with organic ligand, which ligand is the same as or different from that contained in the particular platinum compound, is also advantageous to the present invention.

The amount of these platinum compounds to be used is preferably in the range of 0.00001 to 5 mol, more. preferably 0.005 to 2 mol, per mol of the 1,2-bis(hydrosilyl)benzenes or the 1,2,4,5-tetrakis(hydrosilyl)benzenes. The organic ligand is preferably used in an amount in the range of 1 to 20 mol, more preferably 1 to 4 mol, per mol of the platinum atom.

The reaction of the present invention can be readily carried out, without any solvents, by using a mixture of the 1,2-bis(hydrosilyl)benzenes and the cyclic diynes that are to be interacted, or a mixture of the 1,2,4,5-tetrakis(hydrosilyl )benzenes and the cyclic diynes that are to be interacted. However, use of a solvent does not impair the reaction, and the reaction may be carried out in a solvent if required. The selection of a solvent is made by taking into consideration, for example, the reactivity and the solubility of the 1,2-bis(hydrosilyl)benzenes or the 1,2,4,5-tetrakis(hydrosilyl)benzenes or the cyclic diynes that are to be interacted. The solvent is preferably chosen from generally used solvents, such as hydrocarbon-series solvents and ether-series solvents.

Although, in the production processes of the present invention, the reaction can proceed at 0° C. or below, heating to a temperature of 250° C. is possible, to attain a preferable reaction rate. Depending on the structure of the raw materials, generally a preferable temperature range is 0° to 150° C.

There is no restriction on the reaction time or pressure in the production processes of the present invention. Preferable time period for the reaction is 10 minutes to 100 hours. The reaction can be conducted under ordinary pressure.

Preferably, the reaction in the production processes of the present invention is carried out under an inert gas atmosphere, such as nitrogen, argon, or helium gas.

Isolation of the product after the reaction can easily be carried out by means usually used in organic chemistry, such as usual distillation, recrystallization, chromatography, extraction with a solvent, or reprecipitation.

The molecular weight of the silicon-containing ladder polymer represented by the above formula (V) is preferably in the range of 1,000 to 10,000,000, more preferably 2,000 to 1,000,000, but the present invention is not restricted to these molecular weight ranges.

The end group of the polymer represented by formula (V) may be a hydrogen atom or a triple bond.

By the production method of the second invention, a silicon-containing ladder polymer can be produced wherein the temperature at which the loss in weight by thermogravimetric analysis under a helium atmosphere becomes 5% is 400° C. or more. This silicon-containing ladder polymer itself can be used as a thermal-resistant material or a burning-resistant material.

According to the present invention, a silicon-containing pentacyclic compound represented by formula (III) can be obtained by a one-step reaction from readily available 1,2-bis(hydrosilyl)benzene and cyclic diyne. The compound is useful as a raw material for a burning-resistant material, a thermal-resistant material, or an electrically conductive material.

Since the silicon-containing pentacyclic compound represented by formula (III) is a ladder-type compound, it is greatly improved on the property of thermal resistance, as compared to a compound having a mere chain structure of carbons. The compound represented by formula (III) can be used as a monomer raw-material to produce a thermal-resistant material. For example, a halogen atom, such as a bromine atom, is introduced into both ends of the compound represented by formula (III), and the introduced halogen atoms function as a reaction site, to polymerize this compound.

Further, according to the present invention, a silicon-containing ladder polymer having a complete ladder structure can be obtained by a one-step reaction from readily available 1,2,4,5-tetrakis(hydrosilyl)benzene and cyclic diyne. Those polymers represented by formula (V) are expected to be used as burning-resistant materials, thermal-resistant materials, electrically conductive materials, or nonlinear optical materials. Therefore, the industrial significance of the present invention is great.

The present invention will be described in detail with reference to the following Examples, but the present invention is not restricted to them.

EXAMPLE 1

3.6 Milliliters of a solution of 0.012 mmol of $Pt(CH_2=CH_2)(PPh_3)_2$, 0.56 mmol of 1,2-bis(dimethylsilyl)benzene, and 0.28 mmol of 1,8-cyclotetradecadiin in toluene were reacted for 13 hours at 100° C. under an argon atmosphere. The reaction mixture was separated by thin-layer chromatography, to obtain a compound represented by the following formula, in a yield of 92%:

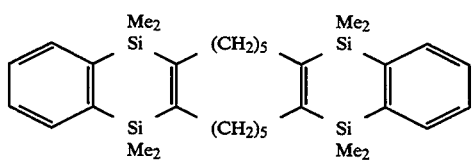

(This compound is a compound represented by formula (III), wherein $R^1$ represents a methyl group, and $R^2$ and $R^3$ each represent a pentamethylene group.)

This compound is a novel compound that does not appear in the literature, and the values of its physical properties and the data on its spectrum were as follows:

Melting point: 191° to 193° C.

$^1$H-NMR (CDCl$_3$): δ0.39 (24H, s), 1.64 (12H, br s), 2.48 (8H, br s), 7.42 (4H, dd, J=3.3, 5.4 Hz), 7.63 (4H, dd, J=3.3, 5.4 Hz), $^{13}$C-NMR (CDCl$_3$): δ−0.29, 26.55, 28.84, 29.83, 128.09, 132.89, 145.27, 152.74, $^{29}$Si-NMR (CDCl$_3$): δ−20.84

IR (KBr): 2946, 1458, 1408, 1245, 1127, 1002, 830, 770, 739, 648 cm$^{-1}$

Elemental analysis: $C_{34}H_{52}Si_4$ Calculated: C 71.25%; H 9.15% Found: C 71.38%; H 9.37%

EXAMPLE 2

0.052 Millimols of 1,2-bis(dimethylsilyl)benzene was added to 1 ml of a solution of 0.052 mmol of $Pt(CH_2=CH_2)(PPh_3)_2$ in toluene, and the mixture was stirred for 15 min at room temperature under a nitrogen atmosphere. Then, 0.026 mmol of 5,6,11,12-tetradehydrodibenzo[a,e]cyclooctene was added and was reacted for 12 hours at room temperature under a nitrogen atmosphere. The reaction mixture was separated by thin-layer chromatography, to obtain a compound represented by the following formula, in a yield of 59%:

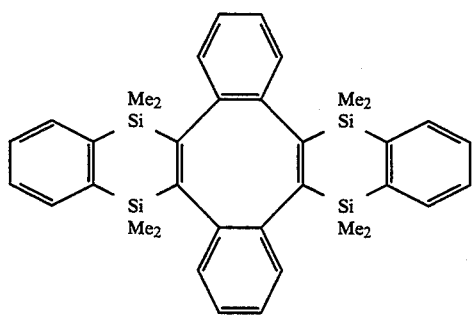

(This compound is a compound represented by formula (III), wherein $R^1$ represents a methyl group, and $R^2$ and $R^3$ each represent a 1,2-phenylene group.)

This compound is a novel compound that does not appear in the literature, and the values of its physical properties and the data on its spectrum were as follows:

Melting point: 226° to 228° C.

$^1$H-NMR (CDCl$_3$): δ0.10 (12H, s), 0.47 (12H, s), 6.93 (4H, dd, J=3.3, 5.9 Hz), 7.02 (4H, dd, J=3.3, 5.9 Hz), 7.32 (4H, dd, J=3.3, 5.4 Hz), 7.52 (4H, dd, J=3.3, 5.4 Hz), $^{13}$C-NMR (CDCl$_3$): δ−1.29, 2.30, 125.06, 126.23, 128.06, 132.65, 142.50, 145.09, 158.63, $^{29}$Si-NMR (CDCl$_3$): δ−20.91

IR (KBr): 3056, 2956, 1468, 1412, 1249, 1125, 990, 897, 864, 832, 812, 775, 739, 687, 652 cm$^{-1}$

Elemental analysis: $C_{36}H_{40}Si_4$ Calculated: C 73.91%; H 6.89% Found: C 73.81%; H 6.85%

EXAMPLE 3

4 Milliliters of a solution of 0.0067 mmol of $Pt(CH_2=CH_2)(PPh_3)_2$, 0.38 mmol of 1,2,4,5-tetrakis(dimethylsilyl)benzene, and 0.38 mmol of 1,8-cyclotetradecadiin in toluene were reacted for 12 hours at 100° C. under an argon atmosphere. The suspension of reaction liquid was poured into methanol (40 ml), and the precipitation was filtered and dried, to obtain a white polymer represented by the following formula, in a yield of 97%:

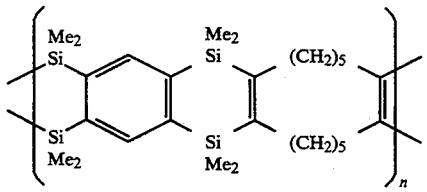

(This polymer is a silicon-containing ladder polymer represented by formula (V), wherein $R^2$ and $R^3$ each represent a pentamethylene group, $R^4$ represents a methyl group, and $R^5$ represents a hydrogen atom.)

This compound is a novel compound that does not appear in the literature, and the values of its physical properties and the data on its spectrum were as follows:

Melting point: 300° C. or over.

Molecular weight: about 3,000 (estimated by end-group determination method by IR)

IR (KBr): 2956, 1251, 828, 764 cm$^{-1}$

Elemental analysis: $(C_{28}H_{46}Si_4)_n$ Calculated: C 67.94 %; H 9.37 % Found: C 67.74 %; H 9.85 %

Thermogravimetric analysis (heating to 900° C. at a heating rate of 10° C./min under a helium atmosphere):

360° C. residual ratio: 99%

435° C. residual ratio: 95%

The above results of thermogravimetric analysis show that the obtained compound may be used as s burning-resistant material or a thermal-resistant material.

Having described our invention as related to the present embodiments, it is our intention that the invention not be limited by any of the details of the description, unless otherwise specified, but rather be construed broadly within its spirit and scope as set out in the accompanying claims.

What we claim is:

1. A method for producing a silicon-containing pentacyclic compound represented by the following formula (III), which method comprises reacting (a) 1,2-bis(hydrosilyl)benzene, represented by the following formula (I), with (b) cyclic diyne, represented by the following formula (II), in the presence of (c) a platinum compound:

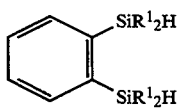 formula (I)

wherein $R^1$ represents a monovalent group;

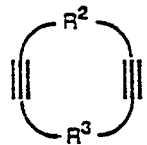 formula (II)

wherein $R^2$ and $R^3$ each represent a divalent group;

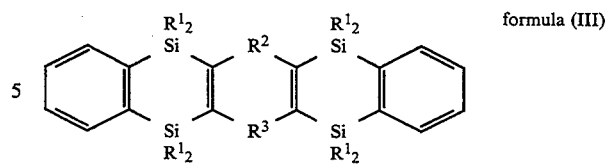 formula (III)

wherein $R^1$, $R^2$, and $R^3$ have the same meanings as defined above.

2. The method as claimed in claim 1, wherein $R^1$ is an alkyl group, an aryl group, an aralkyl group, or an alkoxy group.

3. The method as claimed in claim 1, wherein $R^2$ and $R^3$ are independently selected from the group consisting of an alkylnene group, an arylene group, an aralkylene group, $—CH_2OCH_2—$, $—CH_2CH_2OCH_2CH_2—$, $—CH_2OCH_2CH_2OCH_2—$, $—CH_2OCH_2CH_2OCH_2CH_2OCH_2—$, $—CH_2NRCH_2—$, $—(CH_3)_2Si—O—Si(CH_3)_2—$, and a 1,1'-ferrocenylene group.

4. The method as claimed in claim 1, wherein the molar ratio of the 1,2-bis(hydrosilyl)benzene (a) to the cyclic diyne (b) is in the range of 1:50 to 100:1.

5. The method as claimed in claim 1, wherein the platinum compound (c) is at least, partially soluble in the reaction system.

6. The method as claimed in claim 1, wherein the amount of the platinum compound (c) to be used is in the range of 0.00001 to 5 mol per 1 mol of the 1,2-bis(hydrosilyl)benzene (a).

7. A method for producing silicon-containing ladder polymers represented by the following formula (V), which method comprises reacting (a) 1,2,4,5-tetrakis(hydrosilyl)benzene, represented by the following formula (IV), with (b) cyclic diyne, represented by the following formula (II), in the presence of (c) a platinum compound:

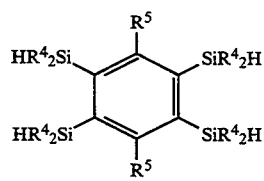 formula (IV)

wherein $R^4$ and $R^5$ each represent a monovalent group;

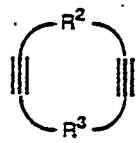 formula (II)

wherein $R^2$ and $R^3$ each represent a divalent group;

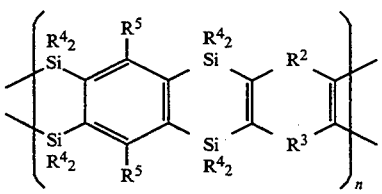 formula (V)

wherein $R^2$, $R^3$, $R^4$, and $R^5$ have the same meanings as defined above, and n is a positive integer.

8. The method as claimed in claim 7, wherein $R^4$ is an alkyl group, an aryl group, or an aralkyl group, and $R^5$ is a hydrogen atom, an alkyl group, an aryl group, an aralkyl group, an alkoxy group, an alkoxymethyl group, or an alkenyl group.

9. The method as claimed in claim 7, wherein $R^2$ and $R^3$ are independently selected from the group consisting of an alkylnene group, an arylene group, an aralkylene group, —$CH_2OCH_2$—, —$CH_2CH_2OCH_2CH_2$—, —$CH_2OCH_2CH_2OCH_2$—, —$CH_2OCH_2CH_2OCH_2CH_2OCH_2$—, —$CH_2NRCH_2$—, —$(CH_3)_2Si$—O—$Si(CH_3)_2$—, and a 1,1'-ferrocenylene group.

10. The method as claimed in claim 7, wherein the molar ratio of the 1,2,4,5-tetrakis(hydrosilyl)benzene (a) to the cyclic diyne (b) is in the range of 1:100 to 200:1.

11. The method as claimed in claim 7, wherein the platinum compound (c) is, at least, partially soluble in the reaction system.

12. The method as claimed in claim 7, wherein the amount of the platinum compound (c) to be used is in the range of 0.00001 to 5 mol per 1 mol of the 1,2,4,5-tetrakis(hydrosilyl)benzene (a).

13. A compound represented by the following formula (III):

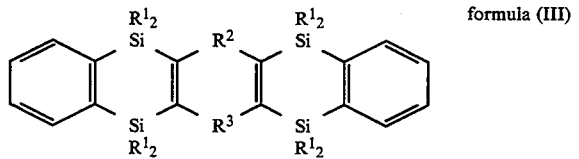

formula (III)

wherein $R^1$ represents a monovalent group, $R^2$ and $R^3$ each represents a divalent group.

14. The compound as claimed in claim 13, wherein $R^1$ is an alkyl group, an aryl group, an aralkyl group, or an alkoxy group.

15. The compound as claimed in claim 13, wherein $R^2$ and $R^3$ are independently selected from the group consisting of an alkylnene group, an arylene group, an aralkylene group, —$CH_2OCH_2$—, —$CH_2CH_2OCH_2CH_2$—, —$CH_2OCH_2CH_2OCH_2$—, —$CH_2OCH_2CH_2OCH_2CH_2OCH_2$—, —$CH_2NRCH_2$—, —$(CH_3)_2Si$—O—$Si(CH_3)_2$—, and a 1,1'-ferrocenylene group.

16. A compound represented by the following formula (V):

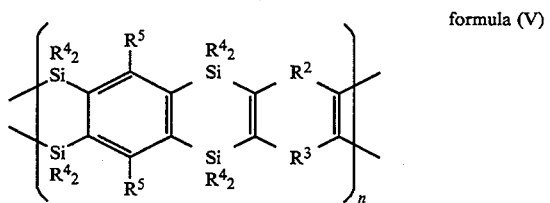

formula (V)

wherein $R^2$ and $R^3$ each represents a divalent group, $R^4$ and $R^5$ each represents a monovalent group, and n is a positive integer.

17. The compound as claimed in claim 16, wherein $R^4$ is an alkyl group, an aryl group, or an aralkyl group, and $R^5$ is a hydrogen atom, an alkyl group, an aryl group, an aralkyl group, an alkoxy group, an alkoxymethyl group, or an alkenyl group.

18. The compound as claimed in claim 16, wherein $R^2$ and $R^3$ are independently selected from the group consisting of an alkylnene group, an arylene group, an aralkylene group, —$CH_2OCH_2$—, —$CH_2CH_2OCH_2CH_2$—, —$CH_2OCH_2CH_2OCH_2$—, —$CH_2OCH_2CH_2OCH_2CH_2OCH_2$—, —$CH_2NRCH_2$—, —$(CH_3)_2Si$—O—$Si(CH_3)_2$—, and a 1,1'-ferrocenylene group.

* * * * *